United States Patent [19]

Brunner et al.

[11] 4,454,773

[45] * Jun. 19, 1984

[54] TIME INTERVAL AUTOMATIC WELL MULTI-PHASE FLUID SAMPLER

[75] Inventors: Paul J. Brunner, Spring, Tex.; Charles A. Christopher, Broken Arrow, Okla.; Robert G. Pindell, Houston, Tex.

[73] Assignee: Texaco Inc., White Plains, N.Y.

[*] Notice: The portion of the term of this patent subsequent to Jun. 19, 2001 has been disclaimed.

[21] Appl. No.: 319,005

[22] Filed: Nov. 6, 1981

[51] Int. Cl.³ .............................................. G01N 1/10
[52] U.S. Cl. ............................ 73/863.31; 73/863.86; 141/236
[58] Field of Search ........... 73/863.31, 863.33, 863.02, 73/863.03, 864.34, 863.81, 863.86; 141/236, 35, 192, 244

[56] References Cited

U.S. PATENT DOCUMENTS

| | | | |
|---|---|---|---|
| 2,677,223 | 1/1954 | Farris | 166/19 |
| 2,728,397 | 12/1955 | Ruska | 166/64 |
| 2,927,641 | 3/1960 | Buck | 166/64 |
| 3,036,229 | 5/1962 | Kemp et al. | 73/863.33 |
| 3,045,750 | 7/1962 | Peters et al. | 166/52 |
| 3,362,222 | 1/1968 | Johnson et al. | 73/863 |
| 4,059,149 | 11/1977 | Harrison | 166/64 |

FOREIGN PATENT DOCUMENTS 917080  1/1963  United Kingdom .............. 73/864.34

Primary Examiner—S. Clement Swisher
Attorney, Agent, or Firm—Robert A. Kulason; Jack H. Park; Henry C. Dearborn

[57] ABSTRACT

An automatic multi-phase well fluid sampler comprises an inlet solenoid valve means on each of a plurality of sample containers for receiving multi-phase well fluid such as a produced oil-water fluid from one of a plurality of wells, and each of the inlet valve means being responsive to a timing and stepping switch means for precisely filling its sample container periodically, in consecutive order, from the same well for providing an improved well sampler system that is more accurate, more precise, more readily adjustable, less complex, discharges less waste oil that damages the environment from the single well, and that indicates the arrival of the multi-phase well fluid at the production well from an injection well and/or the arrival of various chemical concentrations thereof thereafter.

5 Claims, 4 Drawing Figures

TIME INTERVAL AUTOMATIC WELL MULTI-PHASE FLUID SAMPLER

BACKGROUND OF THE INVENTION

Previous to this invention, to get a meaningful fluid sample a person was required to go to the wellhead everytime to get the first fluid sample, wait the required periods of time between samples before getting a second and possibly several thereafter for a meaningful or desired sample or samples. This was very time consuming, costly, and unreliable. It was difficult to achieve, among other problems. These problems prompted the design of the disclosed sampler for automatic capture for analysis produced oil well fluid, for example, at specific time intervals, for detection of injected chemical solutions, for determining the arrival of many chemical species, as polymers, surfactants, tracers, or treating chemicals at the well. The oil sample may likewise be analyzed for the presence of surfactants. Particularly, the time of arrival and the time variation of concentration of the injected chemical solution at the producing well may be determined.

OBJECTS OF THE INVENTION

A primary object of this invention is to provide an improved time interval automatic well fluid sampler that is more accurate, more precise, and more readily adjustable.

Another primary object of this invention is to provide an automatic well fluid sampler having a plurality of containers connected to a well so that the containers may be filled, one after the other, with sample well fluid in consecutive order, periodically, from the same well.

A further primary object of this invention is to provide an automatic multi-phase well fluid sampler for filling a plurality of containers connected to a single well by injecting samples of the multi-phase well fluid into different sample containers from the well in a pre-arranged order other than in consecutive order for security purposes.

A further object of this invention is to provide an automatic well fluid sampler that is easy to operate, is of simple configuration, is economical to build and assemble, and is of greater efficiency for the collection of samples of a multi-phase fluid in consecutive order, periodically, from the same well.

Other objects and various advantages of the disclosed well fluid sampler will be apparent from the following detailed description, together with the accompanying drawings, submitted for purposes of illustration only and not intended to define the scope of the invention, reference being made for that purpose to the subjoined claims.

BRIEF DESCRIPTION OF THE DRAWINGS

The drawings diagrammatically illustrate by way of example, not by way of limitation, one form of the invention wherein like reference numerals designate corresponding parts in the several views in which.

The invention disclosed herein, the scope of which being defined in the appended claims is not limited in its application to the details of construction and arrangement of parts shown and described, since the invention is capable of other embodiments and of being practiced or carried out in various other ways. Also, it is to be understood that the phraseology or terminology employed here is for the purpose of description and not of limitation. Further, many modifications and variations of the invention as hereinbefore set forth will occur to those skilled in the art. Therefore, all such modifications and variations which are within the spirit and scope of the invention herein are included and only such limitations should be imposed as are indicated in the appended claims.

DESCRIPTION OF THE INVENTION

This invention comprises one mechanism for practicing the method of the invention set forth in the co-pending patent application, Ser. No. 319,007, filed on Nov. 6, 1981.

While various devices may be utilized for carrying out or practicing the inventive methods of the above identified patent application, FIGS. 1-4 illustrate at least one, inventive apparatus for practicing the methods described above.

Figure 1:
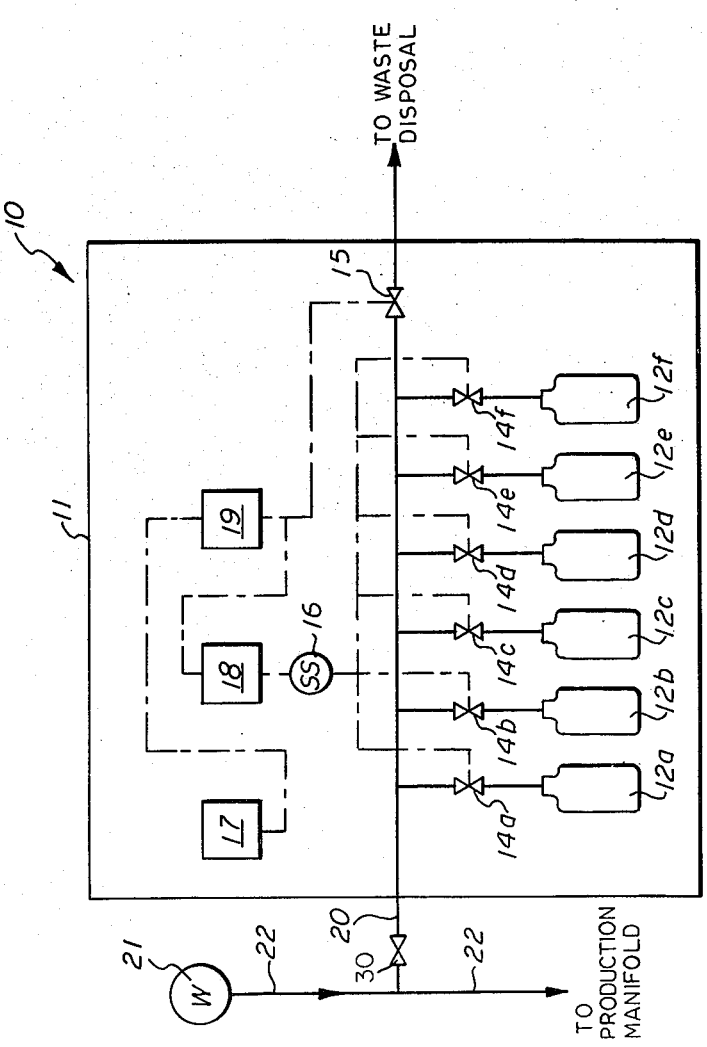
FIG. 1 is a schematic diagrammatic plan view of the time interval automatic well fluid sampler for one of a field of oil wells.

FIG. 1 discloses a schematic diagrammatic plan view of the time interval automatic well fluid sampler 10 for taking fluid samples from any one of a plurality of wells. While this sampler has many uses, it is designed particularly for detecting the precise time of arrival of an injected chemical solution in a particular producing well from an injection well of a field of wells, for example, and/or the precise time of arrival of particular concentrations thereof thereafter. The multi-phase well fluid in our case is preferably a produced oil-water well fluid.

Figure 4:
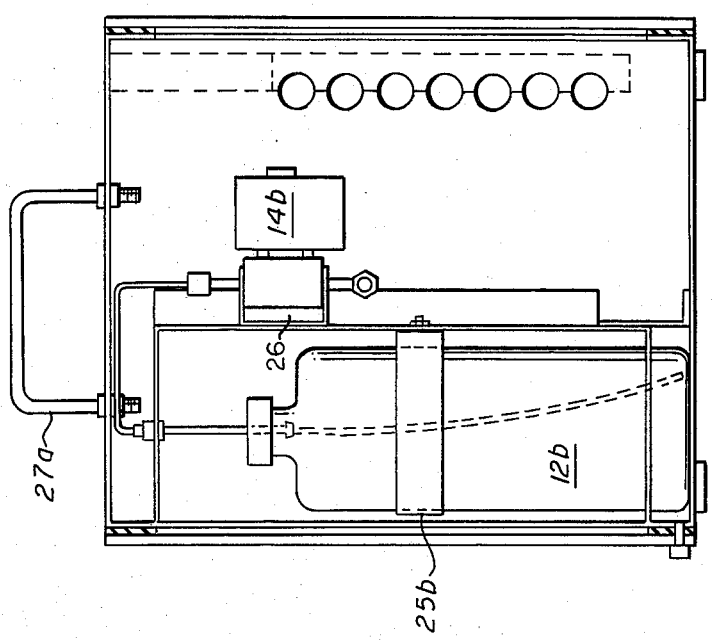
FIG. 4 is a sectional view taken at 4—4 on FIG. 2.
Figure 2:
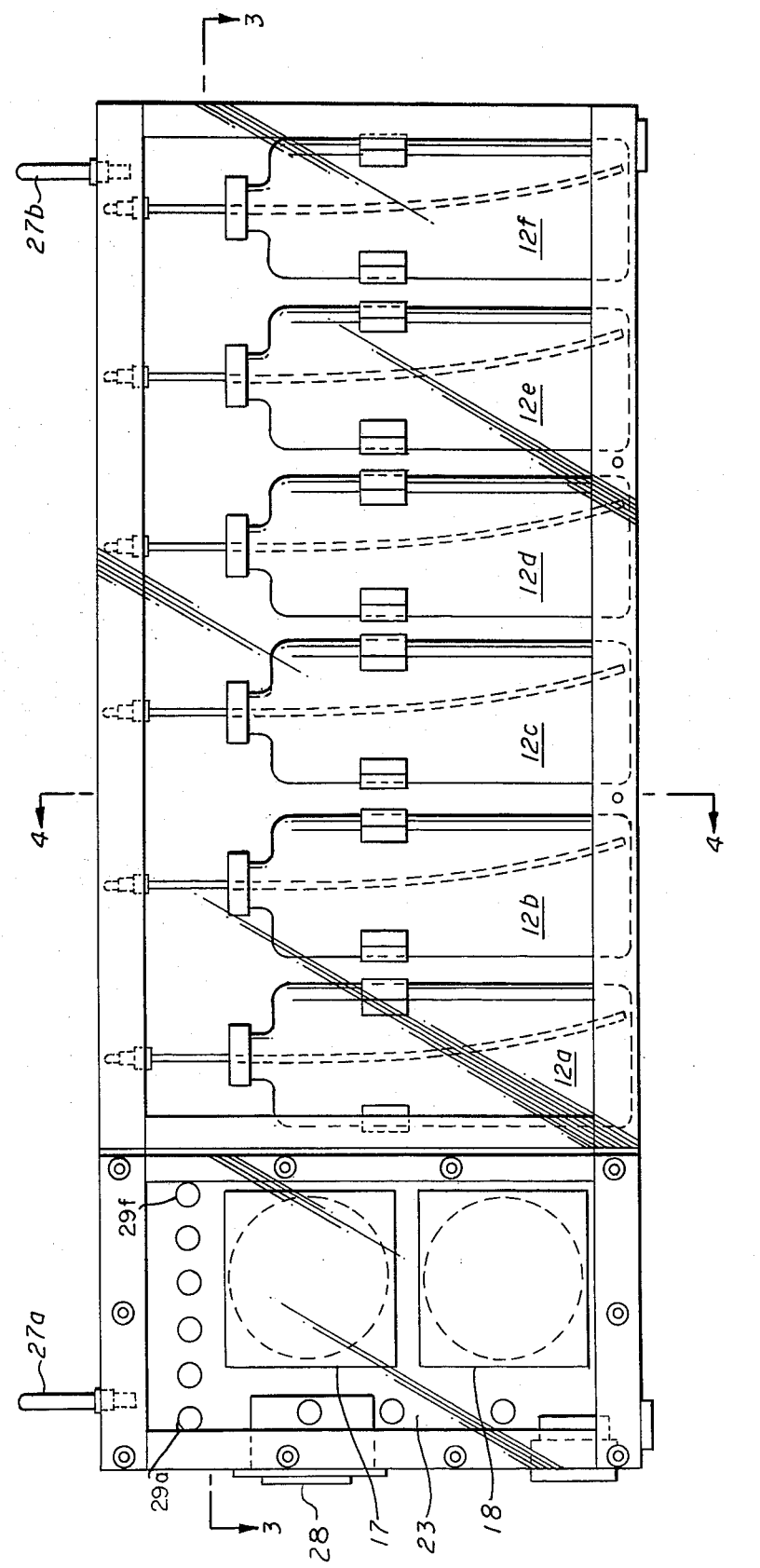
FIG. 2 is a schematic diagrammatic vertical sectional view of the time interval automatic well fluid sampler.
Figure 3:
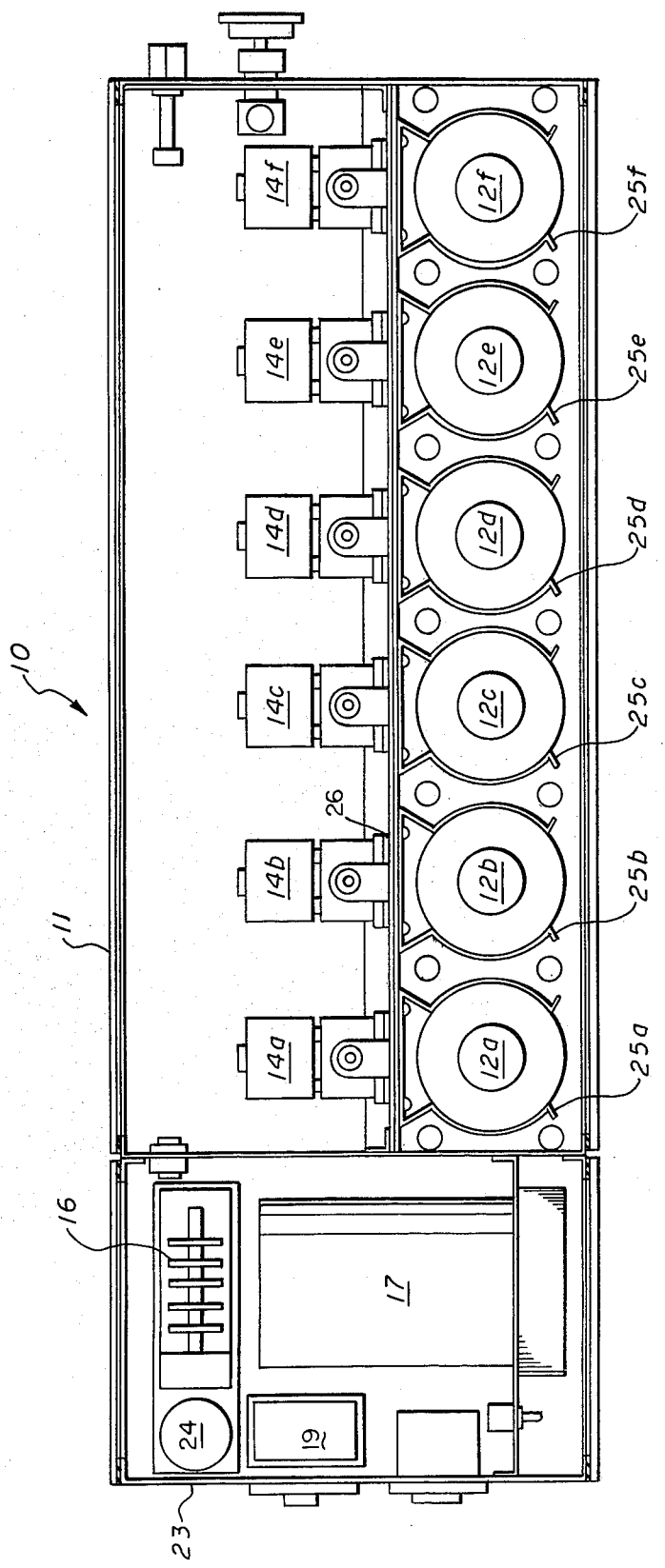
FIG. 3 is a sectional view taken at 3—3 on FIG. 2.

FIGS. 2-4 are enlarged views of the sampler 10.

Sampler 10 illustrated in FIGS. 1-4, comprises a housing 11 enclosing six (6) sample bottles 12a, 12b, 12c, 12d, 12e, and 12f, FIG. 2, and an inlet solenoid valve 14a-14f, FIG. 1, on each of the bottles for controlling its bottle supplied from supply and exhaust line 20. The pressure regulator valve 30 on line 20 always maintains the well fluid entering the sampler at a constant pressure and volume. Another solenoid valve 15 on line 20 purges the piping system of previous fluid prior to sampling. A stepping switch 16 in the electrical control panel box 23, FIG. 2, operates each of the valves in the order desired, as in numerical sequence from one well when awaiting the arrival of an injected chemical tracer or solution, for example, and then after it arrives, determination of the arrival time of the various concentrations may be required from each sample taken thereafter.

Three times are utilized for controlling the flow of well fluid, electronic interval timer 17, FIG. 1, electronic sample timer 18, and time delay relay purging time 19.

Interval timer 17, FIG. 1, controls the time between samples by controlling each respective inlet valve 14a to 14f.

With pressure regulation valve 30 always insuring a constant pressure fluid to the valves, sampler timer 18, FIG. 1, controls each respective inlet valve 14a to 14f for filling its sample bottle 12a to 12f, respectively, exactly with a predetermined amount of well fluid. This is an important feature of the invention. In that respect, if the sample fluids have to be discarded, having a sample only large enough for testing with no extra amount to dispose of means the sample is easier to discard with less pollution of the environment.

Purging timer 19, FIG. 1, controls the main supply and exhaust line 20 from the well 21 which supplies oil to the production manifold 22. Thus, timer 19 purges the main exhaust line 20 by a precise predetermined amount just prior to filling of the next bottle.

FIGS. 2-4 provide more details of the time interval automatic well fluid sampler 10.

FIG. 2, a vertical sectional view of the sampler 10 shows at least two bottles 12b and 12c for receiving a sample each of the well fluid from the one well 21, FIG. 1, and two of the timers, interval timer 17, FIG. 2, and sample timer 18. All conventional electrical wiring between the timers and solenoid valves to permit them to operate as described above is deleted on this FIG. 2 for clarity of disclosure. Exemplary interval timers may be ones set for intervals of 0.1 to 999.9 seconds, 0.1 to 999.9 minutes, or 0.1 to 999.9 hours for plugging in the housing 10, the first being preferred in seconds. Electrical panel 23 is illustrated on the left side of the sampler 10. Carrying handles 27a and 27b are screwed on the top of the sampler 10.

Lights 29a-29f, FIG. 2, indicate which sample bottle is being filled.

FIG. 3, a sectional view at 3—3 on FIG. 2, illustrates the third timer, purge timer 19 on the electrical panel 23. Stepping switch 16 with its accompanying rectifier 24 is mounted to control panel 23 and thus interconnected to the other two timers for operating as described above (interconnections not shown). FIG. 3 likewise shows brackets 25b and 25c for supporting their respective sample bottles 12b and 12c behind which are mounted solenoid valves, one valve each, connected to each bottle, valve 14b being illustrated as mounted to a base plate 26 in housing 11 for filling sample bottle 12b.

FIG. 4, a sectional view at 4—4 on FIG. 2, illustrates sample bottle 12b mounted in the housing 11 with bracket 25b. Solenoid valve 14b is shown mounted to base plate 26 in the housing 11 for being connected to its sample bottle 12b for precisely controlling the filling thereof. An important feature of the invention is that a valve 14b, for example, is responsive to the three timers, 17, 18, and 19. The pressure as well as the volume in the main line 20 from the well being sampled, as well 21, for example, is maintained constant in the housing 11 with pressure regulator valve 30 despite any variations in fluid pressures from the well. Thus the valve is controlled by the timers to close only after the precise amount of well fluid has passed through the valve into the sample bottle.

While only six sample bottles are illustrated, obviously any suitable number may be utilized.

Briefly in operation, after the well fluid supply lines 20 and 22, FIG. 1, are connected to the automatic sampler 10, activation of the main power switch 28, FIG. 2 is accomplished, and the supply line 20 from the well is purged by purging timer operating purging solenoid valve 15 responsive to interval time 17. The desired interval of time is programmed into the interval timer and it signals the sampling timer 18 for beginning to fill the first sample bottle 12a simultaneously with closing of the purging valve 15. When the first sample bottle 12a is filled and the inlet valve 14a FIG. 3, closed, the interval timer 17 delays for its preset time before activating the purging timer 19 for operating the purging valve 15. Then the interval timer 17 indexes the stepping switch 16 one position forward to permit the next or appropriate sample bottle 12b to be filled at the end of the purging cycle. After the proper time delay, the sampling timer 18 activates the next or appropriate solenoid valve 14b for filling sample bottle 12b while simultaneously closing the purging valve 15. Upon precise filling of the second sample bottle 12b, sample timer 18 controls the precise filling of the second sample bottle 12b through solenoid valve mechanism 14b. The instant this second bottle is filled, then interval timer 17 is activated to start on the next timing cycle. This automatic cycling is repeated until the sampler 10 is manually shut down with the main power switch 28, FIG. 2.

Accordingly precise filling or measuring of each sample results in the least amount of sample to dispose of that may damage the environment, an important feature of the invention.

Instead of filling the sample bottles in numerical consecutive order of 12a to 12f, the stepping switch may be preset to another prearranged order other than consecutive order for industrial security purposes, another feature of the invention.

Thus, each of the three interval, sample, and purging timers, 17-19, and the stepping switch 16 may be adjusted or varied for ease of adjustment of various portions of the whole cycle, another feature of the invention.

From the above, accurate timing results in obtaining the periodic samples of a multi-phase fluid product containing chemical species, for example, whose production changes with time, and chemical analysis of the samples provides reservoir description. The arrival of various chemicals in production wells from injection wells may indicate the speed of travel through the formation, among other characteristics.

While the disclosed device of this invention was designed for wellhead sampling, obviously it may be used throughout industry where any other time interval automatic sampling is required.

Obviously other embodiments than that described above, may be utilized in obtaining a precise well sample.

Accordingly, it will be seen that the disclosed time interval automatic well fluid sampler will operate in a manner which meets each of the objects set forth hereinbefore.

While only one mechanism for carrying out the methods of the copending patent application Ser. No. 319,007, filed Nov. 6, 1981, have been disclosed, it will be evident that various other modifications are possible in the arrangement and construction of the disclosed well fluid sampler systems without departing from the scope of the invention and it is accordingly desired to comprehend within the purview of this invention such modifications as may be considered to fall within the scope of the appended claims.

We claim:

1. A time interval automatic well fluid sampler comprising,
   a. a plurality of sample container means for receiving well fluid through a supply line from a single well of a plurality of wells,
   b. inlet valve means for each of said sample container means,
   c. timer means including an interval timer means for controlling each of said inlet valve means, d. each of said inlet valve means being responsive to said interval timer means for filling its sample container means periodically, in consecutive order from said single well at precise time intervals between each filling for improved accuracy and precision of operation for requiring smaller fluid samples, and thus, discharges less waste well fluid that damages the environment, e. said timer means includes purging timer means, and f. said purging timer means being responsive to said interval timer means for starting precisely timed purging of said supply line from said single well prior to the filling of the next consecutive sample container.

2. An automatic well fluid sampler as recited in claim 1 wherein, a. said timer means includes sample timer means, and b. said interval timer means being responsive to said sample timer means for starting the timing period for the filling of the next consecutive sample container means from said single well from the instant of complete filling of the prior sample container means.

3. An automatic well sampler as recited in claim 2 wherein, a. said supply line has a pressure regulating valve means for supplying well fluid at a constant pressure and volume to each of said inlet valve means, and b. said interval timer means being responsive to said sample timer means and said pressure means regulating valve means for starting the timing period for the filling of the next consecutive sample container means to a precise predetermined amount in a period of time relative to said supply line pressure from said single well from the instant of complete filling of the prior sample container means.

4. An automatic well sampler as recited in claim 1 wherein, a. said timer means includes stepping switch means for controlling the sequence of opening of said inlet valve means, and b. each of said inlet valve means being responsive to said stepping switch means for filling its sampler container means in a predetermined sequence other than in numerical consecutive order for industrial security.

5. A time interval automatic multi-phase well fluid sampler comprising, a. timing means for controlling well fluid through a plurality of solenoid inlet valves on a plurality of sample containers from a supply line from a single well of a plurality of wells, b. said solenoid inlet valves being responsive to sad timing means for filling said sample fluid containers periodically, in order from said single well for providing a more accurate well fluid sampler for indicating the arrival time of the multi-phase well fluid and/or the arrival of various concentrations thereof thereafter, for more accurately measuring each fluid sample for conservation of well fluid and thus requiring the discharging of less waste fluid oil that damages the environment from the single well, and c. said timing means includes means for selecting each of said sample container means in other than consecutive order to be filled, periodically, from said single well for industrial security.

* * * * *